United States Patent [19]

De Barbieri

[11] 4,428,875

[45] Jan. 31, 1984

[54] COMPOUNDS OF DICHLORODIETHYLAMINOPHENYLALANINE WITH ANTI-TUMOR ACTIVITY

[75] Inventor: Augusto De Barbieri, Milan, Italy

[73] Assignee: Proter S.p.A., Opera, Italy

[21] Appl. No.: 311,646

[22] Filed: Oct. 15, 1981

Related U.S. Application Data

[63] Continuation-in-part of Ser. No. 173,621, Jul. 30, 1980, Pat. No. 4,314,999, which is a continuation-in-part of Ser. No. 929,372, Jul. 31, 1978, Pat. No. 4,216,208.

[30] Foreign Application Priority Data

Nov. 28, 1980 [IT] Italy .............................. 26305 A/80

[51] Int. Cl.$^3$ ..................... C07C 103/52; A61K 37/02
[52] U.S. Cl. .............................. 260/112.5 R; 424/177
[58] Field of Search .................. 260/112.5 R; 424/177

[56] References Cited

U.S. PATENT DOCUMENTS 4,087,520  5/1978  Braun et al. ................ 260/112.5 R
4,153,688  5/1979  Dimicoli et al. ............. 260/112.5 R Primary Examiner—Blondel Hazel
Attorney, Agent, or Firm—Fisher, Christen & Sabol

[57] ABSTRACT

Compounds with high anti-tumor activity and of moderate toxicity are described which are constituted by tripeptides formed from dichlorodiethylaminophenylalanine, para-fluorophenylalanine and methionine bonded together by peptide links.

The tripeptides of the invention are particularly useful in the treatment of malignant tumors.

6 Claims, No Drawings

COMPOUNDS OF DICHLORODIETHYLAMINOPHENYLALANINE WITH ANTI-TUMOR ACTIVITY

CROSS REFERENCES TO RELATED APPLICATIONS

This application is a continuation-in-part application of my copending application Ser. No. 173,621 filed July 30, 1980 now U.S. Pat. No. 4,314,999, which in turn is a continuation-in-part of my earlier-filed application Ser. No. 929,237 filed July 31, 1978, and now U.S. Pat. No. 4,216,208.

BACKGROUND OF THE INVENTION

The present invention relates to compounds of dichlorodiethylaminophenylalanine which are useful in the treatment of malignant tumours.

Fundamentally this invention is based on the discovery that a tripeptide in which the aminoacid dichlorodiethylaminophenylalanine is bonded, by peptide links, to para-fluorophenylalanine and methionine respectively is highly effective against tumours and is of moderate toxicity.

In the following description, for the purpose of simplification:

MPhe indicates the aminoacid dichlorodiethylaminophenylalanine having the structural formula

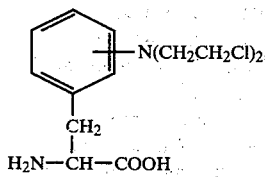

in which the $N(CH_2CH_2Cl)_2$-group may equally well be in the ortho, meta or para position, pFPhe indicates the aminoacid para-fluorophenylalanine having the structural formula:

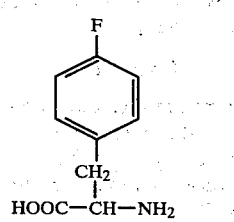

Met indicates the aminoacid methionine of formula:

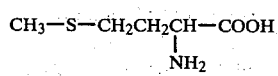

SUMMARY OF THE INVENTION

The results achieved by subsequent systematic research following the said discovery have consistently demonstrated that all the tripeptides formed from the aminoacids specified above have chemotherapeutical activity against tumours and are of limited toxicity, whereby they can all be used to advantage in the treatment of malignant tumours. As a result, the present invention provides a new family of antitumour compounds each of which is characterised in that it comprises the aminoacids dichlorodiethylaminophenylalanine, para-fluorophenylalanine and methionine bonded together by CO—NH— peptide links formed by the respective amino and carboxyl groups of the said aminoacids: the remaining carboxyl group may be esterified.

Thus the invention relates to all the possible permutations of three of the said aminoacids in accordance with the following sequences:

(1) pFPhe. MPhe. Met.
(2) pFPhe. Met. MPhe
(3) MPhe. pFPhe. Met
(4) MPhe. Met. p.FPhe
(5) Met. pFPhe. MPhe.
(6) Met. MPhe. p.FPhe

To advantage, and in accordance with a further characteristic of this invention, the three aminoacids of each anti-tumour compound have a laevo-rotatory (L) configuration in all the sequences specified above.

In the aminoacid dichlorodiethylaminophenylalanine, the $N(CH_2CH_2Cl)_2$— group may, as stated above, be either in the ortho, meta or para position but this group is preferably in the meta position.

Furthermore in several of the sequences listed above, and, more precisely, in sequences 1, 2, 5 and 6, in which the terminal aminoacids are the pFPhe and Met having free $NH_2$ groups, these aminoacids may be formylated.

The preferred process for the preparation of the tripeptides of the invention comprises essentially the steps of:

condensing one of the said aminoacids having a blocked amine group with another of the said aminoacids having a blocked carboxyl group with the aid of dicyclohexylcarbodiimide; —removing one of the blocking groups to form a dipeptide having a blocked amine or carboxyl group; and—condensing the dipeptide with the third aminoacid to form the tripeptide, with the aid of dicyclohexylcarbodiimide. The amine or carboxyl group of the third aminoacid may also be blocked and blocking groups which are not required in the tripeptide to form the compound of the invention are removed in additional steps. Other steps may also be introduced, for example, to form the ester or ester hydrochloride of the tripeptide.

In order to selectively protect the functional amine groups, the amine group is acylated, for example, with formic acid or with carbobenzoxy chloride or with other acylating groups which are known in the art. The carboxyl groups are protected, for example, by esterification in the form of methyl, ethyl, propyl or benzyl esters which are subsequently eliminated by cautious saponification or hydrogenolysis. The invention will be more fully described in the following detailed examples of the preparation of one of the tripeptides of the sequence specified above.

DESCRIPTION OF PREFERRED EMBODIMENTS 1-p-fluoro-L-phenylalanyl-m-di(2-chloroethyl) amino-L-phenylalanyl-L-methionine ethyl ester hydrochloride.

($a_1$)   N-formyl-p-fluoro-L-phenylalanyl-m-di(2-chloroethyl) amino-L-phenylalanine ethyl ester.

51.76 g of m-di(2-chloroethyl) amino-L-phenylalanine ethyl ester were dissolved in 300 ml of tetrahydrofuran and 30.74 g of N-formyl-p-fluoro-L-phenylalanine and 31.7 g of dicyclohexylcarbodiimide were successively added to the solution.

After three hours of agitation, the course of the reaction was checked chromatographically (TLC) (eluent: n-butanol/acetic acid/water=65:15:25 (v/v/v)).

The dicyclohexylurea was removed by filtration and the filtrate was evaporated at reduced pressure at 40° C. to small volume. The residue was taken up in ethyl ether to give: 50 g of crystalline (68%) product ($a_1$) with a melting point of 126° to 127° C.

Analysis: N=8.00% (calculated 7.98%) Cl=13.32% (calculated 13.47%)

($b_1$) N-formyl-p-fluoro-L-phenylalanyl-m-di(2-chloroethyl) amino-L-phenylalanine.

52.6 g of ($a_1$) were dissolved in 260 ml of dimethylformamide (DMF) at about 40° C. The solution was then cooled to ambient temperature and 100 ml of 1 N aqueous sodium hydroxide solution were added over about 30 minutes.

After one hour under agitation the solution was neutralised by the slow addition of 100 ml of 1 N hydrochloric acid. A white product ($b_1$) separated, was filtered and washed with cold water (+5° C.) and finally with ethyl ether.

Yield: 47.3 g (95%) with a melting point of 157° to 159° C.

Analysis: N=8.47% (calculated 8.43%) Cl=14.18% (calculated 14.23%)

($c_1$) L-methionine ethyl ester.

300 g of L-methionine ethyl ester hydrochloride were suspended in a 1 N solution of ammonia in chloroform and kept under agitation for 30 minutes under cold conditions (+5° C.).

The precipitate which formed was filtered and washed with 400 ml of chloroform. The filtrates were united and evaporated at reduced pressure at 40° C. and the residue was taken up with 700 ml of DMF.

The solution contained 1403 moles of methionine ethyl ester, titrated potentiometrically with 0.1 N $HClO_4$.

($d_1$) N-formyl-p-fluoro-L-phenylalanyl-m-di(2-chloroethyl) amino-L-phenylalanyl-L-methionine ethyl ester. 55.4 g of ($b_1$) were dissolved in 450 ml of DMF with slight heating and were subsequently cooled to 15° C.

A solution of: 17.2 g of N-hydroxysuccinimide (HSI) and 25.5 g of dicyclohexylcarbodiimide (DCC) in 50 ml of DMF were prepared separately.

To the solution of ($b_1$) under vigorous agitation were added of the order of: 70 ml of the solution ($c_1$), equivalent to 0.1235 moles of methionine ethyl ester, then the solution of HSI+DCC. The resulting solution was maintained at 10°/15° C. for 30 minutes, then the temperature was allowed to rise to the ambient temperature and agitation was maintained for 16 hours.

Dicyclohexylurea was removed by filtration and washed on the filter with 2×20 ml of DMF.

1800 ml of iced water were added gradually to the united filtrates under agitation so as to maintain the temperature below 20° C.

The product which separated was collected on a filter, washed with water and dried at 40° to 50° C. first in a current of air and then under vacuum over $P_2O_5$.

Yield: 71 g (97.3%) with a melting point of 180°-182° C.

The product obtained was purified by suspension in hot ethyl alcohol and the addition on boiling of a small quantity of DMF until a clear solution was formed.

On cooling a crystalline product was obtained with a melting point of 187°-189° C.

The product ($d_1$) with a melting point of 188°-190° C. was obtained by crystallisation from tetrahydrofuran.

Analysis: N 8.51% (calculated 8.52%) Cl 10.71% (calculated 10.78%) S 4.84% (calculated 4.86%)

($e_1$) p-fluoro-L-phenylalanyl-m-di(2-chloroethyl) amino-L-phenylalanyl-L-methionine ethyl ester hydrochloride.

35.5 g of ($d_1$) were suspended in 500 ml of 1.5 N HCl in ethanol; the mixture was kept under agitation and heated slowly to 60° C. The solution was maintained for 16 hours at ambient temperature and, after a chromatographic (TLC) check, the solution was concentrated at reduced pressure until an oil was formed.

The residue was taken up in ethyl acetate (150 ml) and a saturated aqueous solution of sodium carbonate was added under agitation until the mass had completely dissolved.

The organic phase separated and the aqueous phase was extracted with ethyl acetate (100 ml); the organic extracts were united and washed with 150 ml of cold water and dried with sodium sulphate. The quantity of tripeptide ($e_1$) present in solution was calculated by potentiometric titration with 0.1 N $HClO_4$ in acetic acid.

The solution was evaporated at reduced pressure and the residue was taken up with 250 ml of ethanol. To the solution was added 70 ml of ethanol containing the calculated quantity of HCl.

Crystallisation started within a short time.

After resting for 3 to 4 hours, the crystalline product ($e_1$) was filtered and washed with ethanol, then with ethyl ether and finally dried under vacuum at 80° C. over $P_2O_5$.

Yield: 23.7 g (66%) with a melting point of 180°-182° C.

Analysis: N 8.38% (calculated 8.41%) Cl−5.30% (calculated 5.32%) $Cl_t$ 15.85% (calculated 15.97%) S 4.76% (calculated 4.81%)

EXAMPLE 2

($a_2$) N-formyl-m-di(2-chloroethyl) amino-L-phenylalanyl-L-methionine ethyl ester.

66.6 g of N-formyl-m-di(2-chloroethyl) amino-L-phenylalanine were dissolved in 400 ml of dimethyl formamide (DMF).

To the solution, cooled to 15° C., were added 133 ml of a solution of 0.236 moles of L-methionine ethyl ester in DMF.

Subsequently, still at 15° C., a solution of 31.05 g of N-hydroxysuccinimide and 48.6 g of dicyclohexylcarbodiimide in 100 ml of DMF was added.

After 18 hours of agitation at room temperature, the dicyclohexylurea was removed by filtration and washed on the filter with 2×30 ml of DMF. 2 liters of an ice-water mixture were added to the filtrate under agitation at a rate such as to maintain the temperature below 20° C.

A white precipitate was collected on the filter, washed with water and dried under vacuum at 40° C.

Yield: 90.5 g (92%) with a melting point of 93°-95° C.

Analysis: N=8.49% (calculated 8.53%) Cl=14.44% (calculated 14.41%) S=6.51% (calculated 6.52%)

(b₂) m-di(2-chloroethyl) amino-L-phenylalanyl-L-methionine ethyl ester hydrochloride.

49.2 g of (a₂) were added to 600 ml of a 1.5 N solution of HCl in anhydrous ethyl alcohol. The solution was kept in an Erlenmeyer flask with a ground-glass stopper for 6 hours.

After a chromatographic check (TLC) had revealed the absence of the initial product, the solution was evaporated under reduced pressure at 40° C. until an oily residue was left.

The residue was taken up with 150 ml of cold water (at +5° C.) and a whitish product separated which was dispersed under agitation for 15 minutes; the pH was brought to 3.5 by the addition of an aqueous 10% sodium bicarbonate solution.

The product was collected by filtration, and washed on the filter with cold water. It was dried under vacuum at 40° C. over $P_2O_5$.

Yield: 41.8 g (88.5%) with a melting point of 135°–138° C.

Analysis: N=8.79% (calculated 8.88%) Cl⁻=7.51% (calculated 7.50%) S=6.77% (calculated 6.78%) $Cl_t$=22.39% (calculated 22.79%)

(c₂) m-di-(2-chloroethyl) amino-L-phenylalanyl-L-methionine ethyl ester.

41.8 g of (b₂) were suspended in 120 ml of chloroform and 100 ml of an aqueous 10% sodium bicarbonate solution were added. The mixture was left under agitation for 15 minutes under cold conditions (+5° C.).

The chloroform phase was separated, washed with water, dried, filtered and evaporated under reduced pressure at 40° C.

The oily residue was taken up with 150 ml of tetrahydrofuran.

The solution was titrated potentiometrically with 0.1 N $HClO_4$ in acetic acid. There were 0.083 moles of (c₂) in the solution.

(d₂) p-fluoro-L-phenylalanyl-m-di(2-chloroethyl)-amino-L-phenylalanyl-L-methionine ethyl ester hydrochloride.

To a solution of 17.5 g of N-formyl-p-fluoro-L-phenylalanine in 180 ml of tetrahydrofuran were added solution (c₂) and then 18.5 g of dicyclohexylcarbodiimide. Agitation was maintained for 6 hours and the course of the reaction was checked by TLC.

The dicyclohexylurea was removed by filtration and the filtrate was poured into 1800 ml of cold water (+5° C.). The suspension was brought to a pH of 3.5 with 2 N HCl and, after 15 minutes of agitation under cold conditions, the voluminous white product was collected by filtration and washed on the filter with cold water. The product was dried under vacuum at 40° C. over $P_2O_5$.

Yield: 45.8 g (83%) with a melting point of 180°–182° C.

Analysis: N=8.40% (calculated 8.41%) Cl⁻=5.33% (calculated 5.32%) $Cl_t$=15.89% (calculated 15.97%) S=4.82% (calculated 4.81%)

The chemotherapeutical activity of the compounds (tripeptides) of the invention against tumours was evaluated experimentally by means of two models:

A-Inhibition of the growth of sarcoma 180 by the process established by CCNSC (Cancer Chemotherapy National Service Center U.S. Dept. of Health Education and Welfare, Cancer Chemotherapy Reports No. 25 Dec. 1962).

This test was carried out on Swiss white mice with sarcoma 180 transplanted regularly every week; the sterility of the inoculum was always checked. Aqueous solutions stabilised with carboxymethylcellulose were administered intraperitoneally or subcutaneously on the first, third, fifth and seventh days after the tumour inoculum; on the ninth day the animals were killed and the weight of the tumours, their percentage variation compared to controls, the weight of the spleen and the body weight were measured.

B-Determination of the mean survival time (mean survival time=MST) of $BDF_1$ mice, inoculated intraperitoneally with $10^6$ cells of lymphatic leukemia L1210 taken from regular implants in DBA2 mice. The MST both of controls and of the treated mice was determined and then the increased lifespan (ILS) was determined as set out in "Cancer Chemotherapy Reports" 1972 vol. 3 n 2 (Protocols for Screening Chemical Agents and Natural Products). Against animal Tumors and other biological System—third Edition National Cancer Inst. Bethesda, Md. The compounds were tested by injection intraperitoneally or subcutaneously 24 or 48 hours after the tumour inoculum either in a single massive dose or with fractions of the dose at intervals of 8 days, progressively reduced.

The results of the tests are given in the following table.

The tripeptide pFPhe mMPhe.MetOEtHCl was also tested in AKR mice diagnosed for lymphatic leukemia induced by the Gross leukemia virus. At the very beginning of the test the condition of the leukemic mice was as follows: average weight of the spleen—565 mg per mouse leukemic cells—20,000 per cubic micro-liter.

A single dose of 18–20 mg/kg was injected intraperitoneally or subcutaneously into each mouse. This dose was not found to be toxic for the non-leukemic mice while the treated mice experienced a complete clinical recovery within two days of injection, with normal blood structure, normalization of the thymus and normal spleen with no indication of cellular colonization.

TABLE 1

ACTIVITY OF SOME COMPOUNDS OF THE PRESENT INVENTION ON THE THROW BACK OF SARCOMA 180 ON MOUSE

| | Compounds | Doses in mg/kg | Throw Back % on tumors | Casualties in the treated group |
|---|---|---|---|---|
| 1. | pFPhe.MPhe.Met.Et.HCl | 8 | 85.38 | 0/6 |
| | | 16 | 96.66 | 3/6 |
| 2. | " | 8 | 70.88 | 0/6 |
| | | 16 | 89.51 | 0/6 |
| 3. | " | 8 | 86.47 | 0/6 |
| | | 16 | 97.53 | 3/6 |
| 4. | " | 8 | 62.73 | 0/6 |
| | | 16 | 90.14 | 1/6 |
| 5. | " | 8 | 70.23 | 0/6 |
| | | 16 | 91.21 | 2/6 |
| 6. | " | 8 | 85.00 | 0/6 |
| | | 16 | 93.94 | 1/6 |
| 7. | " | 8 | 79.70 | 0/6 |
| | | 16 | 93.64 | 1/6 |
| 1. | OHO.met.MPhe.pFPhe | 8 | 76.32 | 0/6 |
| | | 16 | 88.04 | 0/6 |
| 2. | " | 8 | 71.33 | 0/6 |
| | | 16 | 73.93 | 0/6 |
| 3. | " | 8 | 74.17 | 0/6 |
| | | 16 | 87.00 | 0/6 |
| 4. | " | 10 | 80.42 | 0/6 |
| | | 16 | 93.89 | 3/6 |
| | | 22 | 96.77 | 3/6 |

What is claimed is:

1. Tripeptide formed from the aminoacids dichlorodiethylaminophenylalanine, para-fluorophenylalanine and methionine bonded together by CO-NH-peptide links.

2. Compound as claimed in claim 1, wherein each said aminoacid has a laevo-rotatory configuration.

3. Compound as claimed in claim 1, wherein said tripeptide comprises a dichlorodiethylaminophenylalanine bonded by peptide links to para-fluorophenylalanine and methionine respectively.

4. Compound as claimed in claim 1, selected from the esters and ester hydrochlorides of said tripeptides.

5. Compound as claimed in claim 1, wherein the terminal aminoacid in said tripeptide having an amine group not bonded in a peptide link is selected from para-fluorophenylalanine and methionine and said amine group is formylated.

6. The compound p-fluoro-L-phenylalanyl-m-di(2-chloroethyl)-amino-L-phenylalanyl-L-methionine ethyl ester hydrochloride.

* * * * *